(12) United States Patent
Drane et al.

(10) Patent No.: US 8,920,803 B2
(45) Date of Patent: Dec. 30, 2014

(54) IMMUNOTHERAPEUTIC METHOD INVOLVING CD123 (IL-3Rα) ANTIBODIES AND IMMUNOSTIMULATING COMPLEX

(75) Inventors: Debra Pauline Drane, Diggers Rest (AU); Eugene Maraskovsky, Parkville (AU); Jefferey Stephen Boyle, Pearcedale (AU)

(73) Assignee: CSL Limited, Parkville (AU)

( * ) Notice: Subject to any disclaimer, the term of this patent is extended or adjusted under 35 U.S.C. 154(b) by 0 days.

(21) Appl. No.: 13/704,583

(22) PCT Filed: Jun. 15, 2011

(86) PCT No.: PCT/AU2011/000725
§ 371 (c)(1),
(2), (4) Date: Feb. 27, 2013

(87) PCT Pub. No.: WO2011/156860
PCT Pub. Date: Dec. 22, 2011

(65) Prior Publication Data
US 2013/0149303 A1    Jun. 13, 2013

Related U.S. Application Data

(60) Provisional application No. 61/354,986, filed on Jun. 15, 2010.

(51) Int. Cl.
| | |
|---|---|
| *A61K 39/00* | (2006.01) |
| *A61K 39/395* | (2006.01) |
| *C12P 21/08* | (2006.01) |
| *C07K 16/28* | (2006.01) |
| *C07K 16/30* | (2006.01) |

(52) U.S. Cl.
CPC ....... *A61K 39/39533* (2013.01); *C07K 16/2866* (2013.01); *A61K 2039/505* (2013.01); *A61K 39/39558* (2013.01); *A61K 2039/55577* (2013.01)
USPC .................. 424/143.1; 424/133.1; 424/153.1; 424/155.1; 530/387.3; 530/388.22; 530/388.7; 530/388.8

(58) Field of Classification Search
None
See application file for complete search history.

(56) References Cited

U.S. PATENT DOCUMENTS

| | | | |
|---|---|---|---|
| 6,177,078 B1 | 1/2001 | Lopez | |
| 6,733,743 B2 * | 5/2004 | Jordan | 424/1.49 |
| 2010/0093003 A1 * | 4/2010 | Jordan | 435/7.23 |

OTHER PUBLICATIONS

Stewart T.J. et al. ISCOMATRIX™ adjuvant: an adjuvant suitable for use in anticancer vaccines. Vaccine, 2004, vol. 22, p. 3738-3743.*

Munoz, L. et al. Interleukin-3 receptor alpha chain (CD123) is widely expressed in hematologic malignancies. Haematologica, 2001, vol. 86, p. 1261-1269.*
Abutalib et al, Monoclonal Antibodies for the Treatment of Acute Myeloid Leukemia, Current Pharmaceutical Biotechnology, 2006, 343-369, 7(5).
Aribi et al, Novel Agents in Acute Meyloid Leukemia, The Cancer Journal, 2006, 77-91, 12(2).
Bagley et al, The Structural and Functional Basis of Cytokine Receptor Activation: Lessons From the Common beta Subunit of the Granulocyte-Macrophage Colony-Stimulating Factor, Interleukin-3 (IL-3), and IL-5 Receptors, Blood, 1997, 1471-1482, 89(5).
Bonnet et al, Human acute myeloid leukemia is organized as a hierarchy that originates from a primitive hematopoietic cell, Nature Medicine, Jul. 1997, 730-737, 3(7).
Budel et al, Interleukin-3 and granulocyte-monocyte colony-stimulating factor receptors on human acute myelocytic leukemia cells and relationship to the proliferative response, Blood, Aug. 1, 1989, 565-571, 74(2).
Delwel et al, Growth regualtion of human acute myeloid leukemia: effects of five recombinant hematopoietic factors in a serum-free culture system, Blood, Dec. 1988, 1944-1949, 72(6).
Graf et al, Expression and prognostic value of hemopoietic cytokine receptors in acute myeloid leukemia (AML): implications for future therapeutical strategies, European Journal of Haematology, 2004, 89-106, 72.
Guan et al, Proliferative status of primitive hematopoietic progenitors from patients with acute myelogenous leukemia (AML), Leukemia, 2000, 2135-2141, 14.
Guzman et al, Nuclear factor-kappa B is constitutively activated in primitive human acute myelogenous leukemia cells, Blood, Oct. 15, 2001, 2301-2307, 98(8).
Hauswirth et al, Expression of the target receptor CD33 in CD34+/CD38−/CD123+AML stem cells, European Journal of Clinical Investigation, 2007, 73-82, 37(1).
Hope et al, Acute myeloid leukemia originates from a hierarchy of leukemic stem cell classes that differ in self-renewal capacity, Nature Immunology, Jul. 2004, 738-743, 5(7).
International Preliminary Report on Patentability for PCT/AU2011/000725, mailed Dec. 19, 2012, six pages.
International Search Report for PCT/AU2011/000725, mailed Jul. 18, 2011, four pages.
Jordan et al, The interleukin-3 receptor alpha chain is a unique marker for human acute myelogenous leukemia stem cells, Leukemia, 2000, 1777-1784, 14.
Lapidot et al, A cell initiating human acute meyloid leukaemia after transplantation into SCID mice, Nature, Feb. 17, 1994, 645-648, 367.
Maraskovsky et al, Development of prophylactic and therapeutic vaccines using the ISCOMATRIX adjuvant, Immunology and Cell Biology, 2009, 371-376, 87.
Miyajima et al, Receptors for granulocyte-macrophage colony-stimulating factor, interleukin-3, and interleukin-5, Blood, Oct. 1, 1993, 1960-1974, 82(7).
Miyauchi, The effects of three recombinant growth factors, IL-3, GM-CSF, and G-CSF, on the blast cells of acute myeloblastic leukemia maintained in short-term suspension culture, Blood, Sep. 1987, 657-663, 70(3).

(Continued)

*Primary Examiner* — Robert Landsman
*Assistant Examiner* — Bruce D Hissong
(74) *Attorney, Agent, or Firm* — Cooley LLP (57) ABSTRACT

A method for the treatment of a condition which is characterized by CD 123-expressing cells in a patient comprises administering to the patient (i) an antibody or antibody fragment which binds selectively to IL-3Rα(CD 123), and (ii) an immunostimulating complex which comprises saponin, a sterol and a phospholipid.

18 Claims, 4 Drawing Sheets

(56) References Cited

OTHER PUBLICATIONS

Morgan et al, Molecularly targeted therapies in myelodysplastic syndromes and acute myeloid leukemias, Ann Hematol, 2006, 139-163, 85.

Riccioni et al, Immunophenotypic Features of Acute Myeloid Leukemias Overexpressing the Interleukin 3 Receptor Alpha Chain, Leukemia & Lymphoma, Aug. 2004, 1511-1517, 45(8).

Sun et al, Monoclonal antibody 7G3 recognizes the N-terminal domain of the human interleukin-3 (IL-3) receptor alpha-chain and functions as a specific IL-3 receptor antagonist, Blood, Jan. 1, 1996, 83-92, 87(1).

Testa et al, Elevated expression of IL-3R alpha in acute myelogenous leukemia is associated with enhanced blast proliferation, increased cellularity, and poor prognosis, Blood, Oct. 15, 2002, 2980-2988, 100(8).

Wang et al, Cancer stem cells: lessons from leukemia, TRENDS in Cell Biology, Sep. 2005, 494-501, 15(9).

Yalcintepe et al, Expression of interleukin-3 receptor subunits on defined subpopulations of acute myeloid leukemia blasts predicts the cytotoxicity of diphtheria toxin interleukin-3 fusion protein against malignant progenitors that engraft in immunodeficient mice, Blood, Nov. 15, 2006, 3530-3537, 108(10).

* cited by examiner

IMMUNOTHERAPEUTIC METHOD INVOLVING CD123 (IL-3Rα) ANTIBODIES AND IMMUNOSTIMULATING COMPLEX

FIELD OF THE INVENTION

This invention relates to an immunotherapeutic method and in particular it relates to a method of immunotherapeutic treatment of conditions which are characterized by CD123-expressing cells, particularly pre-malignant or malignant cancer conditions which express CD123. The invention also extends to products, including kits, for use in such immunotherapeutic treatments, as well as to the use of such products in immunotherapy.

BACKGROUND OF THE INVENTION

Hematological cancer conditions are the types of cancer such as leukemia and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include pre-malignant conditions such as myelodysplastic syndromes (MDS, formerly known as "preleukemia") which are a diverse collection of hematological conditions united by ineffective production (or dysplasia) of myeloid blood cells and risk of transformation to AML.

Leukemic stem cells (LSCs) are cancer cells that possess characteristics associated with normal stem cells, that is, the property of self renewal and the capability to develop multiple lineages. Such cells are proposed to persist in hematological cancers such as AML as distinct populations.[1]

Acute myelogenous leukemia (AML) is a clonal disorder clinically presenting as increased proliferation of heterogeneous and undifferentiated myeloid blasts. The leukemic hierarchy is maintained by a small population of LSCs, which have the distinct ability for self-renewal, and are able to differentiate into leukemic progenitors[1]. These progenitors generate the large numbers of leukemic blasts readily detectable in patients at diagnosis and relapse, leading ultimately to death[2-4]. AML-LSCs have been commonly reported as quiescent cells, in contrast to rapidly dividing clonogenic progenitors[3,5,6]. This property of LSCs renders conventional chemotherapeutics that target proliferating cells less effective, potentially explaining the current experience in which a high proportion of AML patients enter complete remission, but almost invariably relapse, with <30% of adults surviving for more than 4 years[7]. In addition, minimal residual disease occurrence and poor survival has been attributed to high LSC frequency at diagnosis in AML patients[8]. Consequently, it is imperative for the long term management of AML (and similarly other above mentioned hematological cancer conditions) that new treatments are developed to specifically eliminate LSCs[9-14].

AML-LSCs and normal hematopoietic stem cells (HSCs) share the common properties of slow division, self-renewal ability, and surface markers such as the $CD34^+CD38^-$ phenotype. Nevertheless, LSCs have been reported to possess enhanced self-renewal activity, in addition to altered expression of other cell surface markers, both of which present targets for therapeutic exploitation. Interleukin-3 (IL-3) mediates its action through interaction with cell surface receptors that consist of 2 subunits, the a subunit (CD123) and the β common ($β_c$) chain (CD131). The interaction of an a chain with a β chain forms a high affinity receptor for IL-3, and the $β_c$ chain mediates the subsequent signal transduction[15,16]. Over-expression of CD123 on AML blasts, $CD34^+$ leukemic progenitors and LSCs relative to normal hematopoietic cells has been widely reported[17-23], and has been proposed as a marker of LSCs in some studies[24,25]. CD131 was also reported to be expressed on AML cells[21,25] but there are conflicting reports on its expression on AML-LSCs[23,25].

Overexpression of CD123 on AML cells confers a range of growth advantages over normal hematopoietic cells, with a large proportion of AML blasts reported to proliferate in culture in response to IL-3[26-31]. Moreover, high-level CD123 expression on AML cells has been correlated with: the level of IL-3-stimulated STAT-5 activation; the proportion of cycling cells; more primitive cell surface phenotypes; and resistance to apoptosis. Clinically, high CD123 expression in AML is associated with lower survival duration, a lower complete remission rate and higher blast counts at diagnosis[19,21,32].

The increased expression of CD123 on LSCs compared with HSCs presents an opportunity for therapeutic targeting of AML-LSCs. The monoclonal antibody (MAb) 7G3, raised against CD123, has previously been shown to inhibit IL-3 mediated proliferation and activation of both leukemic cell lines and primary cells[33]. However, it has remained unclear whether targeting CD123 can functionally impair AML-LSCs, and whether it can inhibit the homing, lodgment and proliferation of AML-LSCs in their bone marrow niche. Moreover, the relative contributions of direct inhibition of IL-3 mediated signalling versus antibody-dependent cell-mediated cytotoxicity (ADCC) in the ability of 7G3 to target AML-LSCs remain unresolved.

U.S. Pat. No. 6,177,078 (Lopez) discloses the anti-IL-3Receptor alpha chain (IL-3Rα) monoclonal antibody 7G3, and the ability of 7G3 to bind to the N-terminal domain, specifically amino acid residues 19-49, of IL-3Rα. Accordingly, this patent discloses the use of a monoclonal antibody such as 7G3 or antibody fragment thereof with binding specificity for amino acid residues 19-49 of IL-3Rα in the treatment of conditions resulting from an overproduction of IL-3 in a patient (including myeloid leukemias, lymphomas and allergies) by antagonizing the functions of the IL-3.

U.S. Pat. No. 6,733,743 (Jordan) discloses a method of impairing a hematologic cancer progenitor cell that expresses CD123 but does not significantly express CD131, by contacting the cell with a composition of an antibody and a cytotoxic agent (selected from a chemotherapeutic agent, a toxin or an alpha-emitting radioisotope) whereby the composition binds selectively to CD123 in an amount effective to cause cell death. The hematologic cancer may be leukemia or a malignant lymphoproliferative disorder such as lymphoma.

International Patent Publication No. WO 03/055514 (Antigenics Inc.) discloses compositions comprising an immunoreactive reagent and a saponin, and methods of use thereof. The immunoreactive reagent may be an antibody that specifically binds an antigen selected from the group consisting of a tumor-associated antigen, an antigen of an agent of an infectious disease, an antigen associated with a neurodegenerative disease, and an antigen associated with an amyloid disease, and the saponin may be a Quillaja saponin such as QS-7, QS-17, QS-18, QS-21, QS-21-V1 or QS-21-V2.

Bibliographic details of the publications referred to in this specification are referenced at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

SUMMARY OF THE INVENTION

According to the present invention, there is provided a method for the treatment of a condition which is characterized by CD123-expressing cells in a patient, which comprises administering to the patient (i) an antibody or antibody fragment which binds selectively to IL-3Rα (CD123), and (ii) an immunostimulating complex which comprises saponin, a sterol and a phospholipid.

In another aspect, the invention provides the use of (i) an antibody or antibody fragment which binds selectively to IL-3Rα (CD123), and (ii) an immunostimulating complex which comprises saponin, a sterol and a phospholipid, in combination in, or in the manufacture of a product for use in, a method for the treatment of a condition which is characterized by CD123-expressing cells in a patient.

In yet another aspect, the invention also provides a product which comprises (i) an antibody or antibody fragment which binds selectively to IL-3Rα (CD123), and (ii) an immunostimulating complex which comprises saponin, a sterol and a phospholipid, for use in combination in a method for the treatment of a condition which is characterized by CD123-expressing cells in a patient.

In one embodiment, the product may be a kit which comprises, in one or more containers, (i) antibody or antibody fragment which binds selectively to IL-3Rα (CD123), (ii) an immunostimulating complex which comprises saponin, a sterol and a phospholipid, and optionally (iii) instructions for use of said antibody or antibody fragment in combination with said immunostimulating complex in a method for the treatment of a condition which is characterized by CD123-expressing cells in a patient.

In a further aspect, the invention also provides an agent for the treatment of a condition which is characterized by CD123-expressing cells in a patient, which comprises (i) an antibody or antibody fragment which binds selectively to IL-3Rα (CD123), in combination with (ii) an immunostimulating complex which comprises saponin, a sterol and a phospholipid.

Preferably, the patient is a human.

Preferably also, the condition is a haematological cancer condition.

DETAILED DESCRIPTION OF THE INVENTION

In work leading to the present invention, it has been demonstrated that the biological effect of an antibody or antibody fragment which binds selectively to CD123 can be surprisingly enhanced by administration of the antibody or antibody fragment in combination with an immunostimulating complex which comprises saponin, a sterol and a phospholipid.

The present invention provides a method for the treatment of a condition which is characterized by CD123-expressing cells in a patient, which comprises administering to the patient (i) an antibody or antibody fragment which binds selectively to IL-3Rα (CD123), and (ii) an immunostimulating complex which comprises saponin, a sterol and a phospholipid.

The invention also provides the use of (i) an antibody or antibody fragment which binds selectively to IL-3Rα (CD123), and (ii) an immunostimulating complex which comprises saponin, a sterol and a phospholipid, in combination in, or in the manufacture of a product for use in, a method for the treatment of a condition which is characterized by CD123-expressing cells in a patient.

The condition which is treated by the method of the present invention may be a pre-malignant or malignant cancer condition characterized by CD123-expressing cells, more particularly a condition which is characterized by an overabundance of CD123-expressing cells. As used herein, "an overabundance of CD123-expressing cells" includes a level of CD123-expressing cells that is associated with or characteristic of leukemias and other haematological cancer, or that is associated with or characteristic of an elevated risk for leukemias and other haematological cancer.

Preferably, the patient is a human.

Preferably also, the condition is a haematological cancer condition, such as a leukemia.

Reference herein to "treatment" is to be considered in its broadest context, and the term does not necessarily imply that a patient suffering from the relevant condition is treated until recovery from the condition. Accordingly, treatment includes reduction or amelioration of the symptoms of the relevant condition in the patient, as well as halting or at least retarding the progress of, reducing the severity of, or eliminating the condition.

According to the method of the invention, the antibody or antibody fragment is administered to the patient in combination with the immunostimulating complex. As used herein, the expression "in combination" is to be understood as indicating that the antibody or antibody fragment and immunostimulating complex may be administered to the patient simultaneously or sequentially, at the same or different sites in the patient, and by the same or different routes of administration. When administered simultaneously, the antibody or antibody fragment and immunostimulating complex are preferably administered at separate sites.

Thus, the immunostimulating complex may be administered concurrently with the antibody or antibody fragment, or within a short time period before or after the administration of the antibody or antibody fragment, with a time period including, but not limited to, 1, 15 or 30 minutes, or 1, 6 or 12 hours, or even 1, 2 or 5 days.

As used herein, the term "antibody or antibody fragment" refers to an intact immunoglobulin, including monoclonal antibodies, such as chimeric, humanized or human monoclonal antibodies, or to antigen-binding (including, for example, Fv, Fab, Fab' and F(ab')$_2$ fragments) and/or variable-domain-comprising fragments of an immunoglobulin that compete with the intact immunoglobulin for specific binding to the binding partner of the immunoglobulin, e.g. a host cell protein. Regardless of structure, the antigen-binding fragments bind with the same antigen that is recognized by the intact immunoglobulin. Antigen-binding fragments may be produced synthetically or by enzymatic or chemical cleavage of intact immunoglobulins or they may be genetically engineered by recombinant DNA techniques. The methods of production of antigen binding molecules and fragments thereof are well known in the art and are described, for example, in *Antibodies, A Laboratory Manual*, Edited by E. Harlow and D. Lane (1988), Cold Spring Harbor Laboratory, Cold Spring Harbor, N.Y., which is incorporated herein by reference.

Preferably, the antibody is a monoclonal antibody.

In this embodiment of the invention, the antibody may comprise a modified Fc region, more particularly a Fc region which has been modified to provide enhanced effector functions, such as enhanced binding affinity to Fc receptors, antibody-dependent cell-mediated cytotoxicity (ADCC), antibody-dependent cell-mediated phagocytosis (ADCP) and complement-dependent cytotoxicity (CDC). For the IgG class of antibodies, these effector functions are governed by engagement of the Fc region with a family of receptors referred to as the Fcγ receptors (FcγRs) which are expressed on a variety of immune cells. Formation of the Fc/FcγR complex recruits these cells to sites of bound antigen, typically resulting in signalling and subsequent immune responses. Methods for optimizing the binding affinity of the FcγRs to the antibody Fc region in order to enhance the effector functions, in particular to alter the ADCC and/or CDC activity relative to the "parent" Fc region, are well known to persons skilled in the art, and are described, for example, in International Patent Publication No. WO 2009/070844. These methods can include modification of the Fc region of the antibody to enhance its interaction with relevant Fc receptors and increase its potential to facilitate ADCC and ADCP. Enhancements in ADCC activity have also been described following the modification of the oligosaccharide covalently attached to IgG1 antibodies at the conserved $Asn^{297}$ in the Fc region.

The term "binds selectively", as used herein, in reference to the interaction of an antibody or antibody fragment, and its binding partner, e.g. an antigen, means that the interaction is dependent upon the presence of a particular structure, e.g. an antigenic determinant or epitope, on the binding partner. In other words, the antibody or antibody fragment preferentially binds or recognizes the binding partner even when the binding partner is present in a mixture of other molecules or organisms.

The antibody or antibody fragment may be directed to an epitope on CD123 which is involved in IL-3 binding. While not wanting to be bound by any theory, it is believed that such an antibody or antibody fragment would inhibit the ligand/receptor interaction and thereby interfere with IL-3 signal activation and cell viability. Alternatively, the antibody or antibody fragment may be directed to an epitope on CD123 which is not involved in IL-3 binding. While not wanting to be bound by any theory, it is believed that such an antibody or antibody fragment would cause cell death by Fc mediated mechanisms such as ADCC. In yet another alternative, the antibody or antibody fragment may combine both of the above functions.

In one embodiment, the antibody may be the monoclonal antibody (MAb) 7G3, raised against CD123, which has previously been shown to inhibit IL-3 mediated proliferation and activation of both leukaemic cell lines and primary cells (see U.S. Pat. No. 6,177,678 to Lopez). Alternatively, the antibody may be the monoclonal antibody CSL360, a chimeric antibody obtained by grafting the light variable and heavy variable regions of the mouse monoclonal antibody 7G3 onto a human IgG1 constant region (see International Patent Publication No. WO 2009/070844). Like 7G3, CSL360 binds to CD123 (human IL-3Rα) with high affinity, competes with IL-3 for binding to the receptor and blocks its biological activities. CSL360 also has the advantage of potential utility as a human therapeutic agent by virtue of its human IgG1 Fc region which would be able to initiate effector activity in a human setting. Moreover, it is likely that in humans it would show reduced clearance relative to the mouse 7G3 equivalent and be less likely to be immunogenic. Further examples of a suitable antibody include humanised antibody variants of 7G3 or CSL360, fully human anti-CD123 antibodies and anti-CD123 antibodies with enhanced effector function (such as ADCC activity) as described, for example in Example 4 of International Patent Publication No. WO 2009/070844.

Immununostimulating complexes comprising saponin, a sterol such as cholesterol, and a phospholipid such as phosphatidylethanolamine or phosphatidylcholine, formed as typically rigid, hollow, spherical, cage-like particles measuring about 40 nm in diameter are well known in the art as "empty ISCOMs", ISCOM matrix, or more recently as ISCOMATRIX™ adjuvant, and are described, for example, in Pearse M and Drane D, "ISCOMATRIX™ adjuvant for antibody delivery", Adv. Drug Deliv. Rev., 57(2005) 465-474, in Drane D and Pearse M, "The ISCOMATRIX™ adjuvant", in Immunopotentiators in Modern Vaccines, Schijns V E, O'Hagen D T (Eds), Elsevier Academic Press, MA, USA, 191-216 (2006), and in Drane D et al., "ISCOMATRIX™ adjuvant for prophylactive and therapeutic vaccines", *Expert Rev. Vaccines*, 6(5), 761-772 (2007), the contents of which are incorporated herein by reference. Whilst most of the use to date of ISCOMATRIX™ adjuvant has been as an adjuvant in vaccine formulations, ISCOMATRIX™ adjuvant alone, that is in the absence of antigen, has been shown to have potent immunomodulatory effects.

In one aspect, the immunostimulating complex used in accordance with the present invention is ISCOMATRIX™ adjuvant.

The active agents, that is the antibody or antibody fragment and immunostimulating complex, are each administered in an effective amount. An "effective amount" means an amount necessary at least partly to attain the desired therapeutic response. The amount may vary depending upon the age, health and physical condition of the individual to be treated, the racial background of the individual to be treated, the degree of protection desired, the formulation of the composition, the assessment of the medical situation, and other relevant factors. It is expected that the amount will fall in a relatively broad range that can be determined through routine trials. If necessary, the administration of an effective amount may be repeated one or several times. The actual amount administered will be determined both by the nature of the desired therapeutic response and by the rate at which the active agents are being administered.

In accordance with the present invention, the active agents can be administered to the patient by a parenteral route of administration. Parenteral administration includes any route of administration that is not through the alimentary canal (that is, not enteral), including administration by injection, infusion and the like. Administration by injection includes, by way of example, into a vein (intravenous), an artery (intraarterial), a muscle (intramuscular), the peritoneum (intraperitoneal) and under the skin (subcutaneous). In specific embodiments of the present invention, the antibody or antibody fragment can be administered subcutaneously, intravenously, intraperitoneally or intramuscularly, while the immunostimulating complex can be administered subcutaneously or intramuscularly.

Preparations suitable for parenteral administration conveniently comprise a sterile aqueous preparation of the active component which is preferably isotonic with the blood of the recipient. This aqueous preparation may be formulated according to known methods using suitable dispersing or wetting agents and suspending agents. The sterile injectable preparation may also be a sterile injectable solution or suspension in a non-toxic parenterally-acceptable diluent or solvent, or for example as a solution in a polyethylene glycol and lactic acid. Among the acceptable vehicles and solvents that may be employed are water, Ringer's solution, suitable carbohydrates (e.g. sucrose, maltose, trehalose, glucose) and isotonic sodium chloride solution. In addition, sterile, fixed oils are conveniently employed as a solvent or suspending medium. For this purpose, any bland fixed oil may be employed including synthetic mono- or di-glycerides. The formulation of such preparations is well known in the art and is described by way of example in Remington's Pharmaceutical Sciences, 18$^{th}$ Edition, Mack Publishing Company, Pennsylvania, U.S.A.

In another aspect, the present invention provides a product which comprises (i) an antibody or antibody fragment which binds selectively to IL-3Rα (CD123), and (ii) an immunostimulating complex which comprises saponin, a sterol and a phospholipid, for use in combination in a method for the treatment of a condition which is characterized by CD123-expressing cells in a patient.

In this aspect, the product may be a kit which comprises, in one or more containers, (i) an antibody or antibody fragment which binds selectively to IL-3Rα (CD123), (ii) an immunostimulating complex which comprises saponin, a sterol and a phospholipid, and optionally (iii) instructions for use of said antibody or antibody fragment in combination with said immunostimulating complex in a method for the treatment of a condition which is characterized by CD123-expressing cells in a patient.

Each of the components of this kit may be supplied in a separate container, and the instructions, if present, may direct the administration of the components of the kit at the same or different times, at the same or different sites and by the same or different routes of administration.

In yet another aspect, the present invention provides an agent for the treatment of a condition which is characterized by CD123-expressing cells in a patient, which comprises (i) an antibody or antibody fragment which binds selectively to IL-3Rα (CD123), in combination with (ii) an immunostimulating complex which comprises saponin, a sterol and a phospholipid.

The present invention is further illustrated by the following non-limiting examples which show the surprising enhancement of the biological effect of anti-CD123 (IL-3Rα) antibody when it is administered in combination with an immunostimulating complex. The studies in Examples 1 to 4 were carried out in a B16-huCD123$^+$ melanoma model in mice, using the mouse antibody, αIL-3Rα (muCSL360), and ISCOMATRIX™ adjuvant.

EXAMPLE 1

Methods

C57Bl/6 female mice (8 weeks old, 18-20 g weight) were injected with 1×10$^5$ B16-IL3Rα tumor cells on the right flank, subcutaneously in 100 µl sterile PBS at day 0.

On days 2, 9 and 16 mice were treated as:
1—None (n=10)
2—Isotype Control BM4 (n=10)
3—Mouse αIL-3Rα (n=10)
4—ISCOMATRIX™ adjuvant+Isotype Control BM4 (n=10)
5—ISCOMATRIX™ adjuvant+Mouse αIL-3Rα (n=10)
6—ISCOMATRIX™ adjuvant (n=10)

ISCOMATRIX™ adjuvant was administered at 3.8 ISCO Units/mouse in 100 µl sterile PBS, subcutaneously. Mouse αIL-3Rα antibody was administered at 300 µg/mouse in 100 µl sterile PBS, intraperitoneally.

Tumor size was measured every second day and mice were culled when tumor size reached 10×10 mm.

Results

Figure 1:
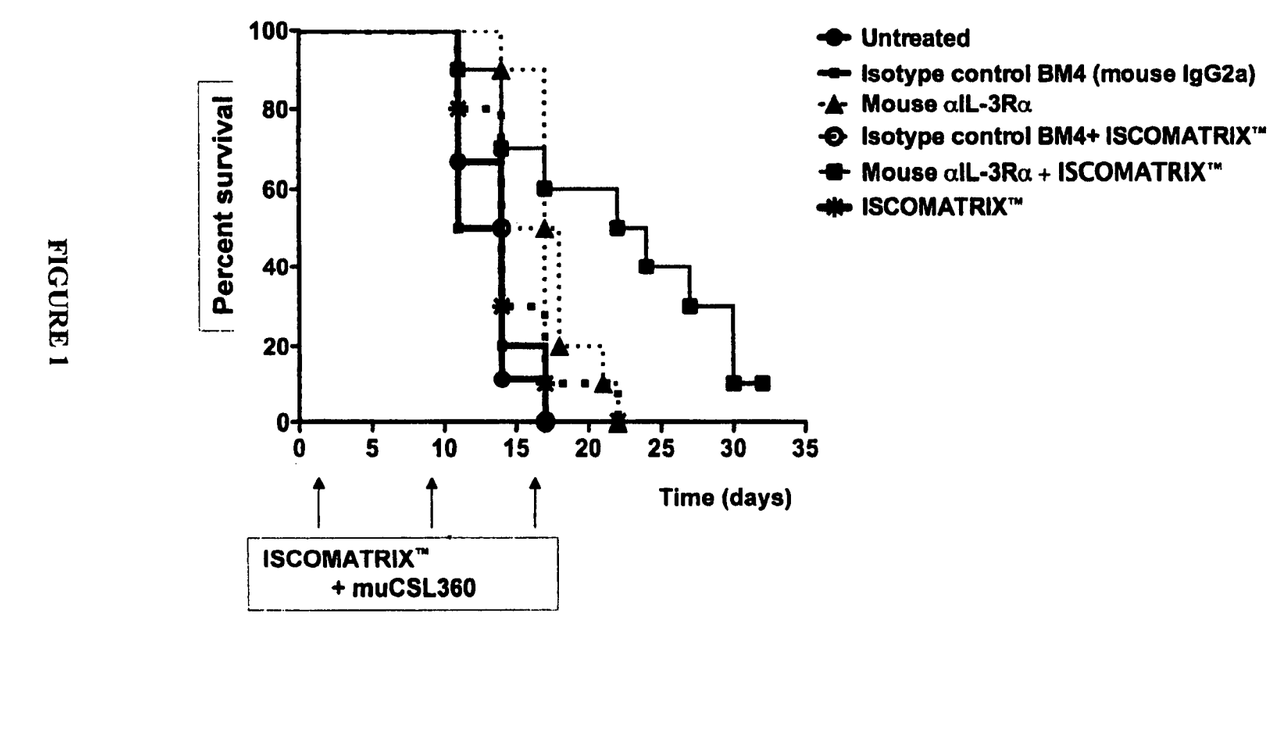
FIG. 1 shows survival rates in the mouse B16-huCD123+ melanoma model ($1\times10^5$ cells) using 300 μg mouse αIL-3Rα±ISCOMATRIX™ adjuvant.

The results are shown in FIG. 1. As shown, all mice that received only the anti-IL-3Rα antibody died by day 22. However, about 10% of the mice receiving both the anti-IL-3Rα antibody and ISCOMATRIX™ adjuvant were still alive by 32 days.

EXAMPLE 2

Methods

Thirty C57Bl/6 female mice (8 weeks old, 18-20 g weight) were injected with 1×10$^4$ B16-IL3Rα tumor cells on the right flank, subcutaneously in 100 µl sterile PBS at day 0.

On days 2, 9 and 16 mice were treated as:
A—Mouse αIL-3Rα (n=10)
B—ISCOMATRIX™ adjuvant+Mouse αIL-3Rα (n=10)
C—Untreated (n=10)

ISCOMATRIX™ adjuvant was administered at 3.8 ISCO Units/mouse in 100 µl sterile PBS, subcutaneously. Mouse αIL-3Rα antibody was administered at 300 µg/mouse in 100 µl sterile PBS, intraperitoneally.

Tumor size was measured every second day and mice were culled when tumor size reached 10×10 mm.

Results

Figure 2:
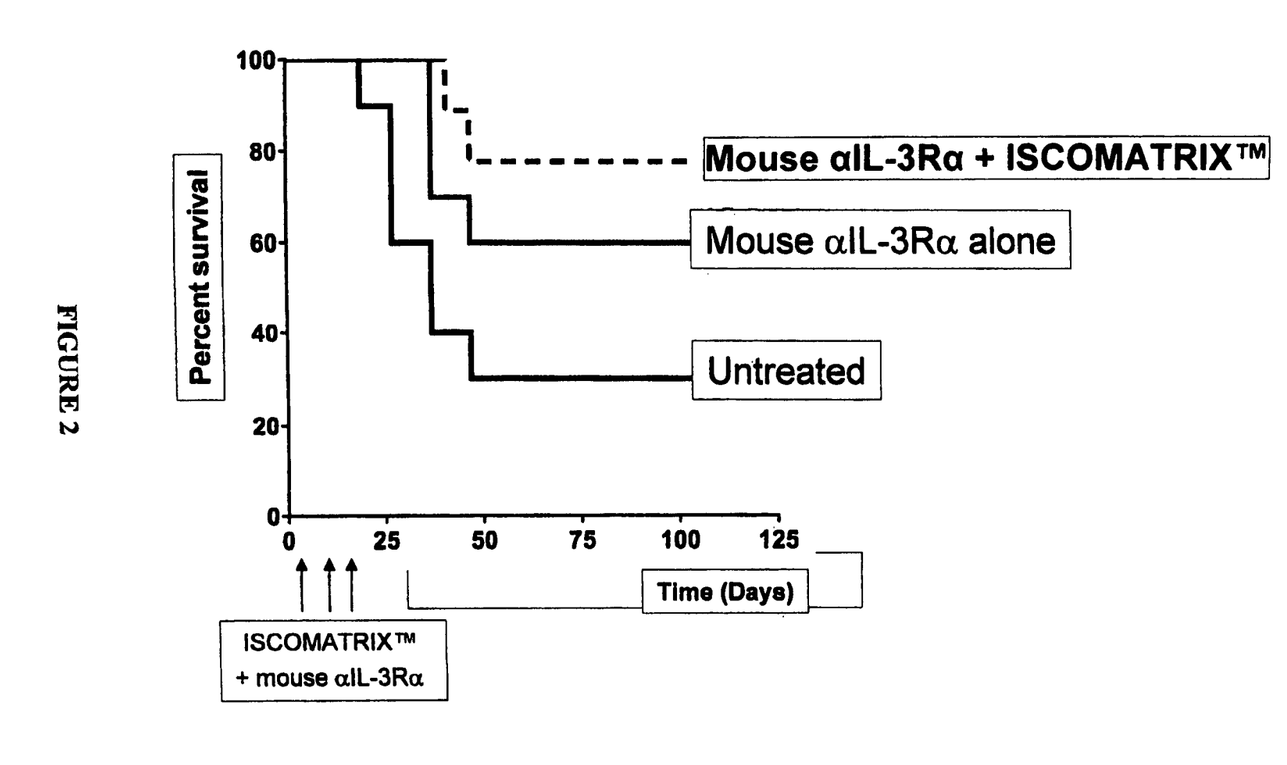
FIG. 2 shows survival rates in the mouse B16-huCD123+ melanoma model ($1\times10^4$ cells) using 300 μg mouse αIL-3Rα±ISCOMATRIX™ adjuvant.

The results are shown in FIG. 2. As shown, when 300 µg/mouse of mouse αIL-3Rα was co-administered with ISCOMATRIX™ adjuvant, the number of mice which survived (i.e. never had a tumor reach a size of 10×10 mm) was significantly higher. Additionally, those mice survived for longer periods of time. FIG. 2 shows that 80% of the mice which received the anti-IL-3Rα antibody and ISCOMATRIX™ adjuvant combination survived, compared to a 60% survival rate for those mice that only received the anti-IL-3Rα antibody.

EXAMPLE 3

Methods

C57Bl/6 female mice (8 weeks old, 18-20 g weight) were injected with 5×10$^5$ B16-IL3Rα tumor cells on the right flank, subcutaneously in 100 µl sterile PBS at day 0.

On days 2, 9 and 16 mice were treated as:
1—None (n=10)
2—Mouse αIL-3Rα (n=10)
3—ISCOMATRIX™ adjuvant+mouse αIL-3Rα (n=8)

ISCOMATRIX™ adjuvant was administered at 3.8 ISCO Units/mouse in 100 µl sterile PBS, subcutaneously. Mouse αIL-3Rα antibody was administered at 50 µg/mouse in 100 µl sterile PBS, intraperitoneally.

Tumor size was measured every second day and mice were culled when tumor size reached 10×10 mm.

Results

Figure 3:
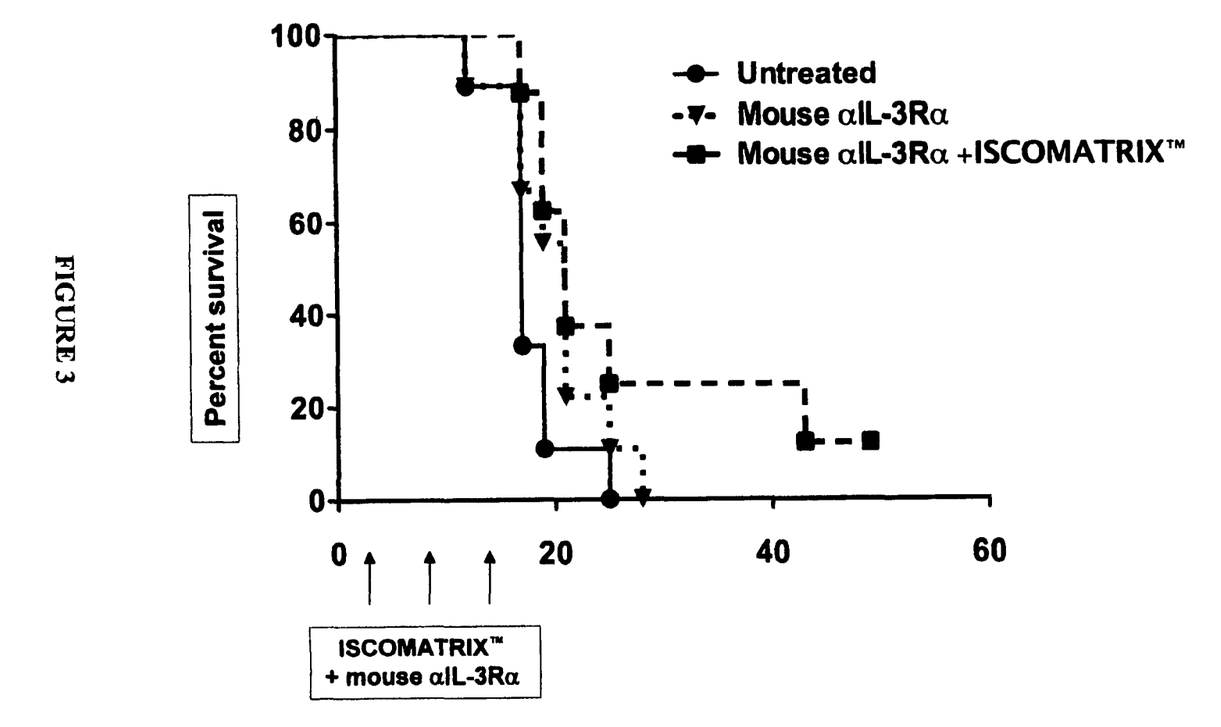
FIG. 3 shows survival rates in the mouse B16-huCD123+ melanoma model ($5\times10^5$ cells) using 50 μg mouse αIL-3Rα±ISCOMATRIX™ adjuvant.

The results are shown in FIG. 3. As shown, mice that only received the anti-IL-3Rα antibody were all dead by day 28. However about 10% of the mice receiving the anti-IL-3Rα antibody and ISCOMATRIX™ adjuvant combination were still alive at about day 50.

EXAMPLE 4

Methods

C57Bl/6 female mice (8 weeks old, 18-20 g weight) were injected with $3 \times 10^4$ B16-IL3Rα tumor cells on the right flank, subcutaneously in 100 μl sterile PBS at day 0.

On days 2, 9 and 16 mice were treated as:
1—None (n=10)
2—Mouse αIL-3Rα (n=10)
3—ISCOMATRIX™ adjuvant+mouse αIL-3Rα (n=10)

ISCOMATRIX™ adjuvant was administered at 3.8 ISCO Units/mouse in 100 μl sterile PBS, subcutaneously. Mouse μIL-3Rα antibody was administered at 100 μg/mouse in 100 μl sterile PBS, intraperitoneally.

Tumor size was measured every second day and mice were culled when tumor size reached 10×10 mm.

Results

Figure 4:
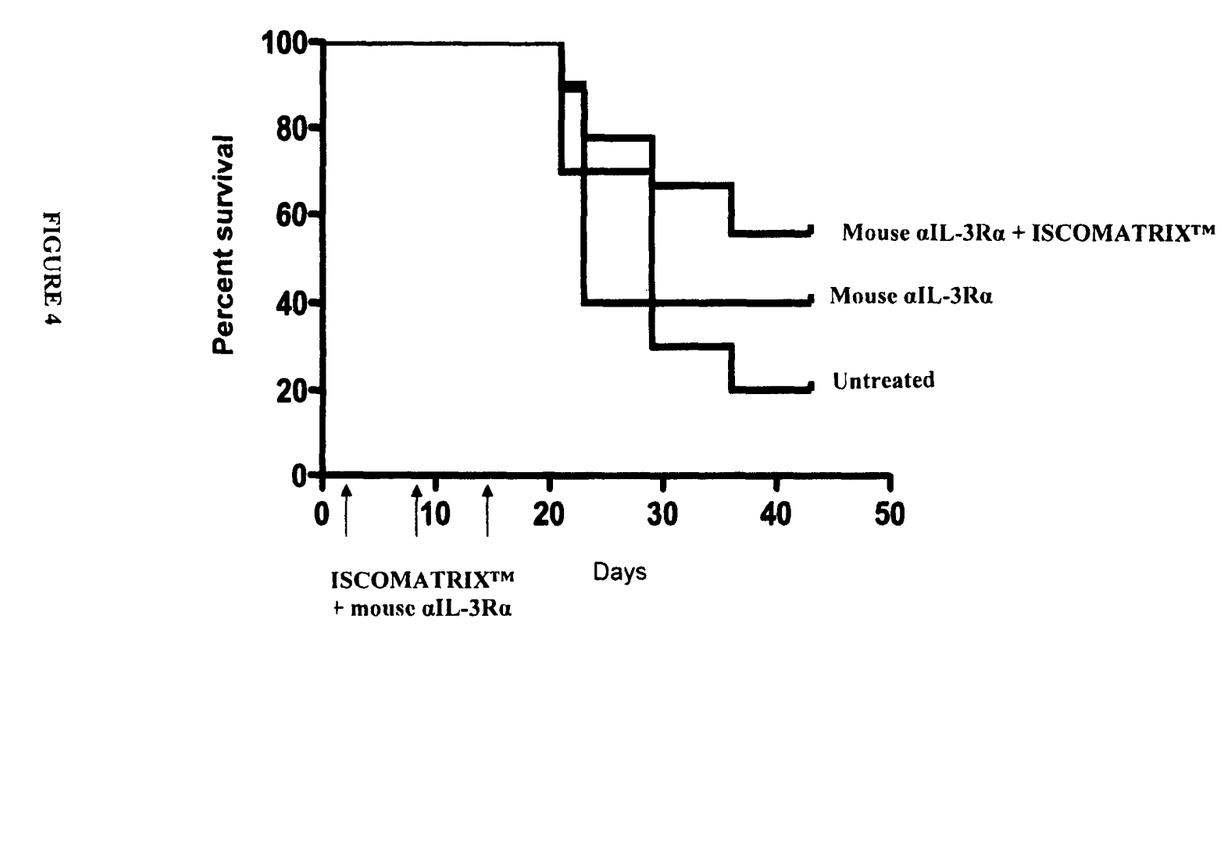
FIG. 4 shows survival rates in the mouse B16-huCD123+ melanoma model ($3\times10^4$ cells) using 100 μg mouse αIL-3Rα±ISCOMATRIX™ adjuvant.

The results are shown in FIG. 4. As shown, about 40% of the mice that only received the anti-IL-3Rα antibody survived at about day 42. However about 55% of the mice receiving the anti-IL-3Rα antibody and ISCOMATRIX™ adjuvant combination were still alive at about day 42.

EXAMPLE 5

Mice are inoculated with either AML-5c (mice are irradiated prior to inoculation) or ALL-19. Mice are then treated in one of the following groups:
1. anti-CD123 antibody in combination with ISCOMATRIX™ adjuvant (subcutaneous neck);
2. IgG1 isotype control and ISCOMATRIX™ adjuvant;
3. anti-CD123 antibody (same antibody as in 1); and
4. IgG1 isotype control.

Treatments are administered weekly for 6 weeks. Following the conclusion of treatment, leukemic burden in peripheral blood (PB) is then monitored weekly.

Measurements of leukemic burden include:
1. Measuring levels of CD45+ cells in PB, wherein the lower the CD45+ cell number, the lower the leukemic burden;
2. Event free survival; and
3. Human engraftment in PB.

EXAMPLE 6

A single-dose biomarker study of a chimeric monoclonal antibody against CD123 (for example, CSL360) in combination with ISCOMATRIX™ adjuvant is carried out in adult Cynomolgus Macaques (n=18), grouped into six groups (Groups 1 to 6) of three animals per group.

Dosage Regimen—Groups 1, 2 and 3:
a. anti-CD123 antibody at 3 dose levels (0.1, 1 and 10 mg/kg, respectively) is administered by intravenous infusion over 15 min on Day 2.

Dosage Regimen—Groups 4, 5 and 6:
a. ISCOMATRIX™ adjuvant (0.5 ml at 150 ISCO Units per mL) is administered by intramuscular injection on Day 1.

b. anti-CD123 antibody at 3 dose levels (0.1, 1 and 10 mg/kg, respectively) is administered by intravenous infusion over 15 min on Day 2.

Blood samples are collected from each animal for haematology and FACS analysis on Day-14 and Day-7 (pre-dose), Day 1 (6 hr post—ISCOMATRIX™ adjuvant injection), Day 2 (6 hr and 12 hr post—anti-CD123 antibody) and Days 3, 4, 9, 12, 16 and 23.

Haematological analysis of these blood samples is carried out using an Advia 120 Haematology Analyzer (Bayer). The samples are also analysed by flow cytometric measurement of basophils, monocytes, pDCs and NK cells.

Serum samples are also collected from each animal for clinical chemistry analysis on Day-14, Day-7, Day 1 (6 hr post-ISCOMATRIX™ adjuvant injection), Day 2 (6 hr post—anti-CD123 antibody) and Day 9. Clinical chemistry analysis of these serum samples is carried out using a Cobas-Integra 400 plus Clinical Chemistry Analyzer (Roche).

Additional serum samples collected from each animal at the same time as the blood samples are processed and then frozen (−70° C.), before further PK and cytokine analysis.

Skin punch biopsies are also taken from each animal at Day-14, Day 4, Day 16 and Day 23, and fixed in formalin for further analysis.

It is to be understood that the detailed description and Examples herein are included solely for the purposes of exemplifying the present invention, and should not be understood in any way as a restriction on the broad description of the invention as set out above. Persons skilled in this art will appreciate that variations and modifications may be made to the invention as broadly described herein, other than those specifically described, without departing from the spirit and scope of the invention. It is to be understood that this invention extends to include all such variations and modifications.

REFERENCES

1. Wang, J. C. & Dick, J. E. Cancer stem cells: lessons from leukemia. *Trends Cell Biol* (2005).
2. Bonnet, D. & Dick, J. E. Human acute myeloid leukemia is organized as a hierarchy that originates from a primitive hematopoietic cell. *Nat Med*, 3, 730-737 (1997).
3. Hope, K. J., Jin, L. & Dick, J. E. Acute myeloid leukemia originates from a hierarchy of leukemic stem cell classes that differ in self-renewal capacity. *Nat Immunol.* 5, 738-743 (2004).
Lapidot, T., et al. A cell initiating human acute myeloid leukaemia after transplantation into SCID mice. *Nature* 367, 645-648 (1994).
5. Guan, Y. & Hogge, D. E. Proliferative status of primitive hematopoietic progenitors from patients with acute myelogenous leukemia (AML). *Leukemia* 14, 2135-2141 (2000).
6. Guzman, M. L., et al. Nuclear factor-kappaB is constitutively activated in primitive human acute myelogenous leukemia cells. *Blood* 98, 2301-2307. (2001).
7. Lowenberg, B., Griffin, J. D. & Tallman, M. S. Acute myeloid leukemia and acute promyelocytic leukemia. *Hematology Am Soc Hematol Educ Program*, 82-101 (2003).
8. van Rhenen, A., et al. High stem cell frequency in acute myeloid leukemia at diagnosis predicts high minimal residual disease and poor survival. *Clin Cancer Res* 11, 6520-6527 (2005).
9. Morgan, M. A. & Reuter, C. W. Molecularly targeted therapies in myelodysplastic syndromes and acute myeloid leukemias. *Ann Hematol* 85, 139-163 (2006).

10. Tallman, M. S. New agents for the treatment of acute myeloid leukemia. *Best Pract Res Clin Haematol* 19, 311-320 (2006).
11. Aribi, A., Ravandi, F. & Giles, F. Novel agents in acute myeloid leukemia. *Cancer J.* 12, 77-91 (2006).
12. Abutalib, S. A. & Tallman, M. S. Monoclonal antibodies for the treatment of acute myeloid leukemia. *Curr Pharm Biotechnol.* 7, 343-369 (2006).
13. Stone, R. M, Novel therapeutic agents in acute myeloid leukemia. *Exp Hematol.* 35, 163-166 (2007).
14. Krug, U., et al. New molecular therapy targets in acute myeloid leukemia. *Recent Results Cancer Res.* 176, 243-262 (2007).
15. Miyajima, A., Mui, A. L., Ogorochi, T. & Sakamaki, K. Receptors for granulocyte-macrophage colony-stimulating factor, interleukin-3, and interleukin-5. *Blood* 82, 1960-1974 (1993).
16. Bagley, C. J., Woodcock, J. M., Stomski, F. C. & Lopez, A. F. The structural and functional basis of cytokine receptor activation: lessons from the common beta subunit of the granulocyte-macrophage colony-stimulating factor, interleukin-3 (IL-3), and IL-5 receptors. *Blood* 89, 1471-1482 (1997).
17. Munoz, L., et al. Interleukin-3 receptor alpha chain (CD123) is widely expressed in hematologic malignancies. *Haematologica* 86, 1261-1269 (2001).
18. Sperr, W. R., et al. Human leukaemic stem cells: a novel target of therapy. *Eur J Clin Invest.* 34 Suppl 2, 31-40 (2004).
19. Graf, M., et al. Expression and prognostic value of hemopoietic cytokine receptors in acute myeloid leukemia (AML): implications for future therapeutical strategies. *Eur J Haematol.* 72, 89-106 (2004).
20. Florian, S., et al. Detection of molecular targets on the surface of CD34+/CD38--stem cells in various myeloid malignancies. *Leuk Lymphoma* 47, 207-222 (2006).
21. Testa, U., et al. Elevated expression of IL-3Ralpha in acute myelogenous leukemia is associated with enhanced blast proliferation, increased cellularity, and poor prognosis. *Blood* 100, 2980-2988 (2002).
22. Riccioni, R., et al. Immunophenotypic features of acute myeloid leukemias overexpressing the interleukin 3 receptor alpha chain. *Leuk Lymphoma* 45, 1511-1517 (2004).
23. Yalcintepe, L., Frankel, A. E. & Hogge, D. E. Expression of interleukin-3 receptor subunits on defined subpopulations of acute myeloid leukemia blasts predicts the cytotoxicity of diphtheria toxin interleukin-3 fusion protein against malignant progenitors that engraft in immunodeficient mice. *Blood* 108, 3530-3537 (2006).
24. Hauswirth, A. W., et al. Expression of the target receptor CD33 in CD34+/CD38–/CD123+ AML stem cells. *Eur J Clin Invest.* 37, 73-82 (2007).
25. Jordan, C. T., et al. The interleukin-3 receptor alpha chain is a unique marker for human acute myelogenous leukemia stem cells. *Leukemia* 14, 1777-1784 (2000).
26. Budel, L. M., Touw, I. P., Delwel, R., Clark, S. C. & Lowenberg, B. Interleukin-3 and granulocyte-monocyte colony-stimulating factor receptors on human acute myelocytic leukemia cells and relationship to the proliferative response. *Blood* 74, 565-571 (1989).
27. Salem, M., et al. Maturation of human acute myeloid leukaemia in vitro: the response to five recombinant haematopoietic factors in a serum-free system. *Br J Haematol.* 71, 363-370 (1989).
28. Delwel, R., et al. Growth regulation of human acute myeloid leukemia: effects of five recombinant hematopoietic factors in a serum-free culture system. *Blood* 72, 1944-1949 (1988).
29. Miyauchi, J., et al. The effects of three recombinant growth factors, IL-3, GM-CSF, and G-CSF, on the blast cells of acute myeloblastic leukemia maintained in short-term suspension culture. *Blood* 70, 657-663 (1987).
30. Pebusque, M. J., et al. Recombinant human IL-3 and G-CSF act synergistically in stimulating the growth of acute myeloid leukemia cells. *Leukemia* 3, 200-205 (1989).
31. Vellenga, E., Ostapovicz, D., O'Rourke, B. & Griffin, J. D. Effects of recombinant IL-3, GM-CSF, and G-CSF on proliferation of leukemic clonogenic cells in short-term and long-term cultures. *Leukemia* 1, 584-589 (1987).
32. Testa, U., et al. Interleukin-3 receptor in acute leukemia. *Leukemia* 18, 219-226 (2004).
33. Sun, Q., et al. Monoclonal antibody 7G3 recognizes the N-terminal domain of the human interleukin-3 (IL-3) receptor alpha-chain and functions as a specific IL-3 receptor antagonist. *Blood* 87, 83-92 (1996).

The invention claimed is:

1. A method for the treatment of a condition which is characterized by CD123-expressing cells in a patient, which comprises administering to the patient a therapeutically effective amount of (i) an antibody or antigen-binding fragment thereof which binds selectively to interleukin 3 receptor alpha (CD123), and (ii) an immunostimulating complex which comprises saponin, a sterol and a phospholipid.

2. The method of claim 1, wherein the patient is a human.

3. The method of claim 1, wherein the condition is a premalignant or malignant cancer condition characterized by CD123-expressing cells.

4. The method of claim 1, wherein the condition is a haematological cancer condition.

5. The method of claim 4, wherein the haematological cancer condition is leukemia.

6. The method of claim 5, wherein the leukemia is acute myelogenous leukemia (AML).

7. The method of claim 1, wherein the immunostimulating complex comprises saponin, cholesterol and a phospholipid selected from the group consisting of phosphatidylethanolamine and phosphatidylcholine.

8. The method of claim 1, wherein the antibody or antigen-binding fragment thereof and immunostimulating complex are administered simultaneously to the patient, either at the same site or at different sites in the patient.

9. The method of claim 1, wherein the antibody or antigen-binding fragment thereof and immunostimulating complex are administered sequentially to the patient, either at the same site or at different sites in the patient.

10. The method of claim 1, wherein the antibody or antigen-binding fragment thereof is a monoclonal antibody, or an antigen-binding and/or variable-domain-comprising fragment thereof.

11. The method of claim 10, wherein the antibody or antigen-binding fragment thereof is a chimeric, humanized or human monoclonal antibody or a fragment thereof.

12. The method of claim 10, wherein the antibody or antigen-binding fragment thereof is a monoclonal antibody comprising a modified Fc region, or a fragment thereof.

13. The method of claim 10, wherein the antibody or an antigen-binding fragment thereof is a monoclonal antibody raised against CD123 or a chimeric or humanized variant thereof, a fully human anti-CD123 antibody, or an anti- CD123 antibody with enhanced effector function, or a antigen-binding fragment thereof.

14. The method of claim 1, wherein the antibody or antigen-binding fragment thereof is administered subcutaneously, intravenously, intraperitoneally or intramuscularly.

15. The method of claim 1, wherein the immunostimulating complex is administered subcutaneously or intramuscularly.

16. A product which comprises (i) an antibody or antigen-binding fragment thereof which binds selectively to IL-3Rα (CD123), and (ii) an immunostimulating complex which comprises saponin, a sterol and a phospholipid, for use in combination in a method for the treatment of a condition which is characterized by CD123-expressing cells in a patient.

17. The product of claim 16, which is a kit which comprises, in one or more containers, (i) an antibody or antigen-binding fragment thereof which binds selectively to IL-3Rα (CD123), (ii) an immunostimulating complex which comprises saponin, a sterol and a phospholipid, and optionally (iii) instructions for use of said antibody or antibody fragment in combination with said immunostimulating complex in a method for the treatment of a condition which is characterized by CD123-expressing cells in a patient.

18. An agent for the treatment of a condition which is characterized by CD123-expressing cells in a patient, which comprises (i) an antibody or antigen-binding fragment thereof which binds selectively to IL-3Rα (CD123), in combination with (ii) an immunostimulating complex which comprises saponin, a sterol and a phospholipid.

* * * * *